United States Patent
Bourne et al.

(10) Patent No.: US 8,282,542 B2
(45) Date of Patent: *Oct. 9, 2012

(54) FLATTENED TUBULAR MESH SLING AND RELATED METHODS

(75) Inventors: George Bourne, Southborough, MA (US); Leonard Pinchuk, Miami, FL (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 391 days.

This patent is subject to a terminal disclaimer.

(21) Appl. No.: 12/391,995

(22) Filed: Feb. 24, 2009

(65) Prior Publication Data
US 2009/0156893 A1 Jun. 18, 2009

Related U.S. Application Data

(63) Continuation of application No. 11/314,284, filed on Dec. 20, 2005, now Pat. No. 7,513,865.

(51) Int. Cl.
*A61F 2/02* (2006.01)

(52) U.S. Cl. ........................................................ 600/30

(58) Field of Classification Search .................. 600/29, 600/30, 37; 606/151, 154, 157
See application file for complete search history.

(56) References Cited

U.S. PATENT DOCUMENTS

| | | |
|---|---|---|
| 3,124,136 A | 3/1964 | Usher |
| 3,272,204 A | 9/1966 | Artandi et al. |
| 3,372,696 A | 3/1968 | Rudie |
| 4,347,847 A | 9/1982 | Usher |
| 4,452,245 A | 6/1984 | Usher |
| 4,585,458 A | 4/1986 | Kurland |
| 4,986,831 A | 1/1991 | Kino et al. |
| 5,147,374 A | 9/1992 | Fernandez |
| 5,178,630 A | 1/1993 | Schmitt |
| 5,234,457 A | 8/1993 | Anderson |
| 5,358,492 A | 10/1994 | Feibus |
| 5,368,602 A | 11/1994 | de la Torre |
| 5,500,000 A | 3/1996 | Feagin et al. |
| 5,686,090 A | 11/1997 | Schilder et al. |
| 5,919,232 A | 7/1999 | Chaffrinoeon et al. |
| 5,954,057 A | 9/1999 | Li |
| 6,042,592 A | 3/2000 | Schmitt |
| 6,099,547 A | 8/2000 | Gellman et al. |
| 6,200,330 B1 | 3/2001 | Benderev et al. |
| 6,375,662 B1 | 4/2002 | Schmitt |
| 6,506,190 B1 | 1/2003 | Walshe |
| 6,648,921 B2 | 11/2003 | Anderson et al. |

(Continued)

FOREIGN PATENT DOCUMENTS

EP 0643945 3/1995

(Continued)

OTHER PUBLICATIONS

Cruikshank, S.H., et al., "Anterior Vaginal Wall Culdeplasty at Vaginal Hysterectomy to CB Prevent Posthysterectomy Anterior Vaginal Wall Prolapse," Am. J. Obstet. GynecoL, 174:1863-1872 (1996).

(Continued)

*Primary Examiner* — Christine Matthews
(74) *Attorney, Agent, or Firm* — Bingham McCutchen LLP

(57) ABSTRACT

The invention generally relates to surgically implantable supportive slings. More specifically, in various embodiments, the invention is directed to multilayer mesh slings formed from a tubular mesh material.

11 Claims, 2 Drawing Sheets

U.S. PATENT DOCUMENTS

| | | |
|---|---|---|
| 6,652,450 B2 | 11/2003 | Neisz et al. |
| 6,666,817 B2 | 12/2003 | Li |
| 6,669,706 B2 | 12/2003 | Schmitt et al. |
| 6,808,486 B1 | 10/2004 | O'Donnell |
| 6,852,330 B2 | 2/2005 | Bowman et al. |
| 6,911,003 B2 | 6/2005 | Anderson et al. |
| 2002/0099258 A1 | 7/2002 | Staskin et al. |
| 2003/0065402 A1 | 4/2003 | Anderson et al. |
| 2003/0171644 A1 | 9/2003 | Anderson et al. |
| 2003/0191480 A1 | 10/2003 | Ulmsten et al. |
| 2003/0225424 A1 | 12/2003 | Benderev |
| 2004/0015044 A1 | 1/2004 | Zappala |
| 2004/0106847 A1 | 6/2004 | Benderev |
| 2004/0111100 A1 | 6/2004 | Benderev et al. |
| 2004/0122474 A1 | 6/2004 | Gellman et al. |
| 2004/0144395 A1 | 7/2004 | Evans et al. |
| 2005/0004576 A1 | 1/2005 | Benderev |
| 2005/0038451 A1* | 2/2005 | Rao et al. ............ 606/151 |
| 2005/0070930 A1 | 3/2005 | Kammerer |
| 2005/0107660 A1 | 5/2005 | Valtchev |
| 2005/0123581 A1* | 6/2005 | Ringeisen et al. ........ 424/423 |
| 2005/0191331 A1 | 9/2005 | Hunter et al. |
| 2005/0234291 A1 | 10/2005 | Gingras |
| 2005/0283040 A1 | 12/2005 | Greenhaigh |

FOREIGN PATENT DOCUMENTS

| | | |
|---|---|---|
| EP | 0692225 | 1/1996 |
| EP | 1306061 | 5/2003 |
| FR | 02859624 | 3/2005 |
| WO | WO-00/74594 | 12/2000 |
| WO | WO-02/30293 | 4/2002 |
| WO | WO-02/069781 | 9/2002 |
| WO | WO-2005/094721 | 10/2005 |

OTHER PUBLICATIONS

Hakim, S., et al., "Use of Biodegradable Mesh as a Transport for a Cultured Uroepithelial Graft: An Improved Method UsinQ CollaQen Gel," UroloQY, 44(1):139-142 (1994).

Kovac, S.R., et al., "PUbic Bone Suburethral Stabilization Sling for Recurrent Urinary Incontinence," Obstetrics &Gynecology, 89(4):624-627 (1997).

Matapurkar, B.G., et aL, "A New Technique of 'Marlexe-Perltoneal Sandwich' in the Repair of Large Incisional Hernias," World J. Surg., 15:768-770 (1991).

Olsen, L., et aL, "Urethral Reconstruction With a New Synthetic Absorbable Device," Scand. J. Urol. Nephrol., 26:323-326 (1992).

Stamey, Thomas, "Endoscopic Suspension of the Vesical Neck for Urinary Incontinence in Females," SurQ, 192(4):465, (1980).

* cited by examiner

FLATTENED TUBULAR MESH SLING AND RELATED METHODS

CROSS-REFERENCE TO RELATED APPLICATION

This application is a continuation of U.S. patent application Ser. No. 11/314,284 filed on Dec. 20, 2005, the entire contents of which are incorporated herein by reference.

FIELD OF THE INVENTION

The invention generally relates to surgically implantable supportive slings. More specifically, in various embodiments, the invention is directed to flattened tubular mesh slings and related methods of use and fabrication.

BACKGROUND

Urinary incontinence affects over 13 million men and women of all ages in the United States. Stress urinary incontinence (SUI) affects primarily women and is generally caused by two conditions, intrinsic sphincter deficiency (ISD) and hypermobility. These conditions may occur independently or in combination. In ISD, the urinary sphincter valve, located within the urethra, fails to close properly (coapt), causing urine to leak out of the urethra during stressful activity. Hypermobility is a condition in which the pelvic floor is distended, weakened, or damaged, causing the bladder neck and proximal urethra to rotate and descend in response to increases in intra-abdominal pressure (e.g., due to sneezing, coughing, straining, etc.). The result is that there is an insufficient response time to promote urethral closure and, consequently, urine leakage and/or flow results.

These and related conditions are often treated using an implantable supportive sling. Such slings may be made from a variety of materials, but are often made from a cut sheet of mesh material. The mesh is typically knit in bulk and cut to both a suitable length and a suitable width, which is labor intensive. Additionally, cutting the slings to a suitable width can leave tanged jagged edges along the length of the sling. In some instances, such tangs may cause tissue irritation subsequent to or during sling placement. Further, the mesh sheets are prone to stretching, twisting and otherwise deforming during placement within the body of a patient.

Accordingly, there is a need for an improved surgically implantable sling or sling-like support, which does not require being cut to particular widths, which may be easily formed without tanged or jagged edges, and which is less prone to undesirable deformation during implantation.

SUMMARY OF THE INVENTION

The invention addresses the deficiencies of the prior art by providing an improved implantable sling for supporting an anatomical site in the body of a patient. More particularly, in various aspects, the invention provides a supportive sling formed initially from a tubular mesh material, along with methods of making and using such a sling. According to one embodiment, the tubular mesh material may be knitted, woven, braided or formed in any other suitable manner. Subsequent to formation, the tube is flattened into a two layer mesh strip. The flattening process may include, for example, pressing and/or heating. In some embodiments, the two mesh layers are flattened into contact with each other. However, in other embodiments, the flattening process acts to set the mesh so that the two mesh layers may not move relative to each other. In some instances, the heat and/or pressure is sufficient to set the mesh. However, in some embodiments, an adhesive may be applied between the two mesh layers to set or aid in setting the mesh so that the two layers do not move relative to each other. In still another embodiment, individual fibers comprising the mesh may be coated with an adhesive, which may help to maintain the porosity of the sling. According to a further embodiment, subsequent to the mesh being flattened, it may be cut in any desirable length for implantation into the body of a patient.

According to various configurations, pores/interstitial gaps are formed between the fibers of the mesh sling. In one embodiment, the pores between the fibers are greater than about 50 micrometers (μm) subsequent to flattening. According to a further embodiment, the fibers used to form the mesh tube have a diameter of between about 5 μm and about 1,000 μm. In an alternate embodiment, the fibers used to form the mesh tube have a diameter of between about 50 μm and about 1,000 μm, which leads to a sling thickness of between about 0.1 mm and about 2 mm. In some instances, the fibers have a diameter of between about 100 μm and about 500 μm, leading to a sling thickness of between about 0.2 mm and about 1 mm. According to various constructions, the flattened sling may have a width of between about 0.5 cm to about 1 cm, about 1 cm to about 4 cm, about 4 cm to about 6 cm, about 6 cm to about 8 cm, or larger, depending on the anatomical location to be supported.

The sling may be fabricated from any of a plurality of biocompatible materials, such as nylon, silicone, polyethylene, polyester, polyethylene, polyurethane, polyimide, polypropylene, polyethylene terephthalate (PET), fluoropolymers, copolymers thereof, combinations thereof, or other suitable synthetic material(s). According to one feature, the sling material is absorbable by the patient's body. According to some embodiments, the sling material may be derived from mammalian tissue(s), synthetic tissue(s), or a combination of mammalian tissue(s) and synthetic material(s). The sling fibers may be formed from one or more filaments, which may be made from one or more materials, or may be formed as monofilaments. The sling may incorporate or be coated with one or more agents to provide a therapeutic effect, for example, to reduce discomfort, to reduce the chance of infection and/or to promote tissue growth. According to some embodiments, the one or more agents may be disposed between the sling fibers and/or between the two sling layers, and/or disposed to surround the sling fibers.

According to one configuration, the sling includes a film placed between the two sling layers prior to flattening. The film may, for example, contain the one or more therapeutic agents for release into the body subsequent to sling implantation.

These and other features, advantages and aspects of the invention are described below with respect to the various illustrative embodiments of the invention.

BRIEF DESCRIPTION OF THE DRAWINGS

Various illustrative embodiments of the invention are described below with reference to the appended drawings, which may not be drawn to scale and in which like parts are designated by like reference designations.

DESCRIPTION OF ILLUSTRATIVE EMBODIMENTS

As described in summary above, in various illustrative embodiments, the invention is directed to a multilayer implantable sling formed from a flattened tubular mesh material. By forming the implantable sling from the flattened tubular mesh material, the process of cutting slings to desired widths can be avoided. Additionally, slings with smooth, rather than tanged or jagged, long edges can be easily formed, without the need for any additional detanging or smoothing process.

Figure 1A:
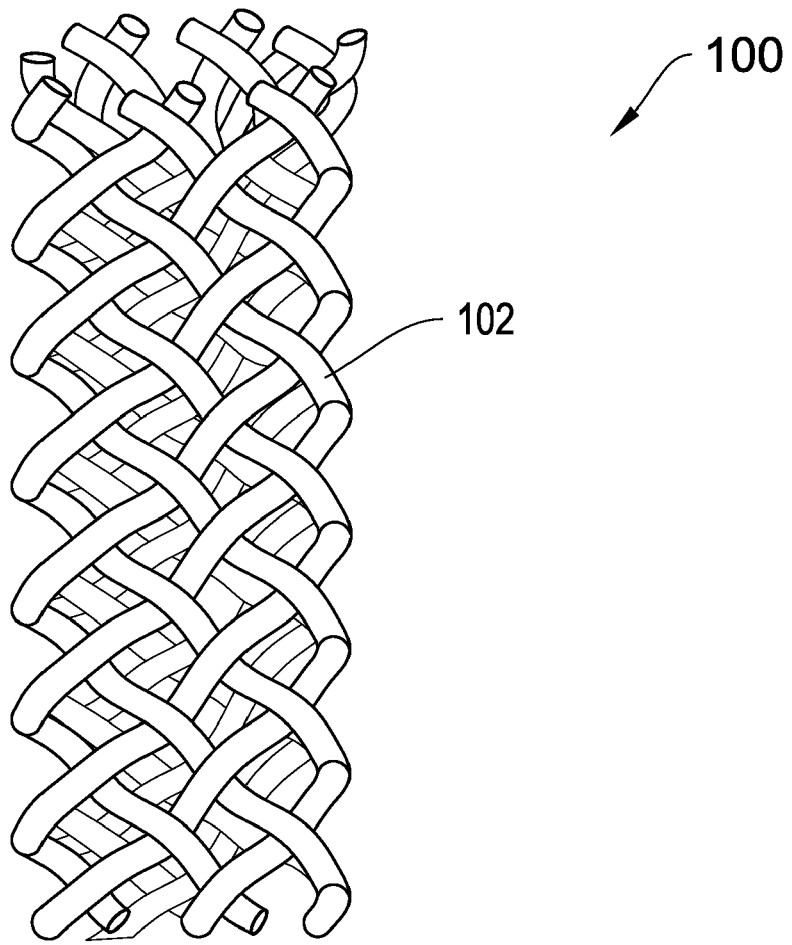
FIG. 1A is a top view of an exemplary tubular mesh material of the type employed to create a two layer implantable mesh sling according to an illustrative embodiment of the invention.
Figure 1B:
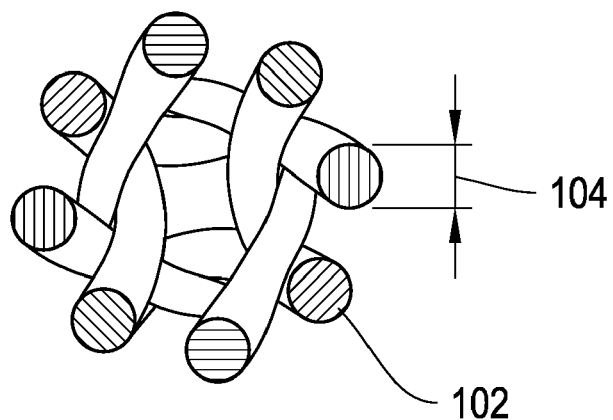
FIG. 1B is an end view of the tubular mesh material of FIG. 1A.

FIG. 1A is a top view of a tubular mesh material 100 of the type that may be employed in forming a supporting implantable sling of the invention. FIG. 1B shows an end view of the tubular material 100 of FIG. 1. Referring to both FIGS. 1A and 1B, the mesh material 100 includes a plurality of fibers 102 that are braided, knitted or otherwise woven together into a tubular configuration. The mesh material 100 may be configured into a porous tubular configuration. The mesh material 100 may be non-woven, such as a mat material. According to the illustrative embodiment, the fibers 102 have approximately equal outside diameters 104. However, this need not be the case. The outside diameters 104 of the fibers 102 are, for example, between about 50 µm and about 1000 µm. In some illustrative embodiments, the fibers 102 have outside diameters of between about 0.1 mm and about 0.5 mm.

The fibers 102 may be formed as mono- or multi-filament fibers. In the case of the multi-filament fibers, the filaments may all be fabricated from the same material, or single fibers may included filaments of differing materials. In the case of monofilament fibers, all of the fibers of the mesh may be fabricated from the same material, or fibers of differing materials may be combined to form the mesh tube 100.

Exemplary mesh materials include, for example, synthetic materials, natural materials (e.g., biological) or a combination thereof. The mesh may be fabricated from any of a number of biocompatible materials, such as nylon, silicone, polyethylene, polyester, polyethylene, polyimide, polyurethane, polypropylene, fluoropolymers, copolymers thereof, combinations thereof, or other suitable synthetic material(s). The material may be, for example, a biodegradable synthetic material. The term "biodegradable," as used herein, refers to the property of a material that dissolves in the body. Such materials may also be absorbed into the body, i.e., bioabsorbable.

Suitable bioabsorbable synthetic materials include, without limitation, polylactic acid (PLA), polyglycolic acid (PGA), poly-L-lactic acid (PLLA), human dermis and decellularized animal tissue. Human tissues may be derived, for example, from human cadaveric or engineered human tissue. Animal tissues may be derived, for example, from porcine, ovine, bovine, and equine tissue sources. The material may be an omnidirectional material, a material that has equivalent tensile strength from any direction, such as pericardium or dermis. Alternatively, the material may be an oriented material, a material that has a single direction where the tensile strength of the material is the highest. Oriented materials may include rectus fascia and/or facia lata, as well as oriented synthetic materials.

Exemplary biodegradable polymers, which may be used to form the tubular mesh 100, in addition to those listed above, include, without limitation, polylactic acid, polyglycolic acid and copolymers and mixtures thereof, such as poly(L-lactide) (PLLA), poly(D,L-lactide) (PLA), polyglycolic acid [polyglycolide (PGA)], poly(L-lactide-co-D,L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), poly(D,L-lactide-co-caprolactone) (PLA/PCL), and poly(glycolide-co-caprolactone) (PGA/PCL); polyethylene oxide (PEO); polydioxanone (PDS); polypropylene fumarate; polydepsipeptides, poly(ethyl glutamate-co-glutamic acid), poly(tert-butyloxy-carbonylmethyl glutamate); polycaprolactone (PCL), poly(hydroxy butyrate), polycaprolactone co-butylacrylate, polyhydroxybutyrate (PHBT) and copolymers of polyhydroxybutyrate; polyphosphazenes, poly(phosphate ester); maleic anhydride copolymers, polyiminocarbonates, poly[(97.5% dimethyl-trimethylene carbonate)-co-(2.5% trimethylene carbonate)], cyanoacrylate, hydroxypropylmethylcellulose; polysaccharides, such as hyaluronic acid, chitosan, alginates and regenerate cellulose; poly(amino acid) and proteins, such as gelatin and collagen; and mixtures and copolymers thereof.

The tubular mesh 100, either as a whole or on a fiber 102 by fiber 102 basis, may include an agent for release into the patient's tissues. One illustrative agent is a tissue growth factor that promotes, when applied to the patient's tissues in a pharmaceutically acceptable amount, well-organized collagenous tissue growth, such as scar tissue growth, preferably, in large quantities. According to one feature, the agent may or may not block or delay the dissolvability of the biodegradable materials. This may be controlled by selecting differing methods for loading the agent onto the sling. The tissue growth factor may include natural and/or recombinant proteins for stimulating a tissue response so that collagenous tissue such as scar tissue growth is enhanced. Exemplary growth factors that may be used include, but are not limited to, platelet-derived growth factor (PDGF), fibroblast growth factor (FGF), transforming growth factor-beta (TGF-beta), vascular endothelium growth factor (VEGF), Activin/TGF and sex steroid, bone marrow growth factor, growth hormone, Insulin-like growth factor 1, and combinations thereof. The agent may also include a hormone, including but not limited to estrogen, steroid hormones, and other hormones to promote growth of appropriate collagenous tissue such as scar tissue. The agent may also include stem cells or other suitable cells derived from the host patient. These cells may be fibroblast, myoblast, or other progenitor cells to mature into appropriate tissues. Besides applying active pharmaceutical agents, passive agents may be applied to promote tissue ingrowth. For example, titanium sputtering or chrome sputtering can be used.

In various illustrative embodiments, the agent may include one or more therapeutic agents. The therapeutic agents may be, for example, anti-inflammatory agents, including steroidal and non-steroidal anti-inflammatory agents, analgesic agents, including narcotic and non-narcotic analgesics, local anesthetic agents, antispasmodic agents, growth factors, gene-based therapeutic agents, and combinations thereof.

Exemplary steroidal anti-inflammatory therapeutic agents (glucocorticoids) include, but are not limited to, 21-acetoxyprefnenolone, aalclometasone, algestone, amicinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumehtasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol priopionate, halometasone, halopredone acetate, hydrocortamate, hydrocortisone, loteprednol etabonate, mazipredone, medrysone, meprednisone, methyolprednisolone, mometasone furoate, paramethasone, prednicarbate, prednisolone, prednisolone 25-diethylaminoacetate, prednisone sodium phosphate, prednisone, prednival, prednylidene, rimexolone, tixocortal, triamcinolone, triamcinolone acetonide, triamcinolone benetonide, triamcinolone hexacetonide, and pharmaceutically acceptable salts thereof.

Exemplary non-steroidal anti-inflammatory therapeutic agents include, but are not limited to, aminoarylcarboxylic acid derivatives such as enfenamic acid, etofenamate, flufenamic acid, isonixin, meclofenamic acid, mefanamic acid, niflumic acid, talniflumate, terofenamate and tolfenamic acid; arylacetic acid derivatives such as acemetacin, alclofenac, amfenac, bufexamac, cinmetacin, clopirac, diclofenac sodium, etodolac, felbinac, fenclofenac, fenclorac, fenclozic acid, fentiazac, glucametacin, ibufenac, indomethacin, isofezolac, isoxepac, lonazolac, metiazinic acid, oxametacin, proglumetacin, sulindac, tiaramide, tolmetin and zomepirac; arylbutyric acid derivatives such as bumadizon, butibufen, fenbufen and xenbucin; arylcarboxylic acids such as clidanac, ketorolac and tinoridine; arylpropionic acid derivatives such as alminoprofen, benoxaprofen, bucloxic acid; carprofen, fenoprofen, flunoxaprofen, flurbiprofen, ibuprofen, ibuproxam, indoprofen, ketoprofen, loxoprofen, miroprofen, naproxen, oxaprozin, piketoprofen, pirprofen, pranoprofen, protizinic acid, suprofen and tiaprofenic acid; pyrazoles such as difenamizole and epirizole; pyrazolones such as apazone, benzpiperylon, feprazone, mofebutazone, morazone, oxyphenbutazone, phenybutazone, pipebuzone, propyphenazone, ramifenazone, suxibuzone and thiazolinobutazone; salicylic acid derivatives such as acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamine o-acetic acid, salicylsulfuric acid, salsalate and sulfasalazine; thiazinecarboxamides such as droxicam, isoxicam, piroxicam and tenoxicam; others such as ε-acetamidocaproic acid, s-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole and tenidap; and pharmaceutically acceptable salts thereof.

Exemplary narcotic analgesic therapeutic agents include, but are not limited to, alfentanil, allylprodine, alphaprodine, anileridine, benzylmorphine, bezitramide, buprenorphine, butorphanol, clonitazene, codeine, codeine methyl bromide, codeine phosphate, codeine sulfate, desomorphine, dextromoramide, dezocine, diampromide, dihydrocodeine, dihydrocodeinone enol acetate, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, hydrocodone, hydromorphone, hydroxypethidine, isomethadone, ketobemidone, levorphanol, lofentanil, meperidine, meptazinol, metazocine, methadone hydrochloride, metopon, morphine, myrophine, nalbuphine, narceine, nicomorphine, norlevorphanol, normethadone, normorphine, norpipanone, opium, oxycodone, oxymorphone, papaveretum, pentazocine, phenadoxone, phenazocine, pheoperidine, piminodine, piritramide, proheptazine, promedol, properidine, propiram, propoxyphene, rumifentanil, sufentanil, tilidine, and pharmaceutically acceptable salts thereof.

Exemplary non-narcotic analgesic agents that may be combined with the slings of the invention include, but are not limited to, aceclofenac, acetaminophen, acetaminosalol, acetanilide, acetylsalicylsalicylic acid, alclofenac, alminoprofen, aloxiprin, aluminum bis(acetylsalicylate), aminochlorthenoxazin, 2-amino-4-picoline, aminopropylon, aminopyrine, ammonium salicylate, amtolmetin guacil, antipyrine, antipyrine salicylate, antrafenine, apazone, aspirin, benorylate, benoxaprofen, benzpiperylon, benzydamine, bermoprofen, brofenac, p-bromoacetanilide, 5-bromosalicylic acid acetate, bucetin, bufexamac, bumadizon, butacetin, calcium acetylsalicylate, carbamazepine, carbiphene, carsalam, chloralantipyrine, chlorthenoxazin(e), choline salicylate, cinchophen, ciramadol, clometacin, cropropamide, crotethamide, dexoxadrol, difenamizole, diflunisal, dihydroxyaluminum acetylsalicylate, dipyrocetyl, dipyrone, emorfazone, enfenamic acid, epirizole, etersalate, ethenzamide, ethoxazene, etodolac, felbinac, fenoprofen, floctafenine, flufenamic acid, fluoresone, flupirtine, fluproquazone, flurbiprofen, fosfosal, gentisic acid, glafenine, ibufenac, imidazole salicylate, indomethacin, indoprofen, isofezolac, isoladol, isonixin, ketoprofen, ketorolac, p-lactophenetide, lefetamine, loxoprofen, lysine acetylsalicylate, magnesium acetylsalicylate, methotrimeprazine, metofoline, miroprofen, morazone, morpholine salicylate, naproxen, nefopam, nifenazone, 5' nitro-2' propoxyacetanilide, parsalmide, perisoxal, phenacetin, phenazopyridine hydrochloride, phenocoll, phenopyrazone, phenyl acetylsalicylate, phenyl salicylate, phenyramidol, pipebuzone, pipervlone, prodilidine, propacetamol, propyphenazone, proxazole, quinine salicylate, ramifenazone, rimazolium metilsulfate, salacetamide, salicin, salicylamide, salicylamide o-acetic acid, salicylsulfuric acid, salsalte, salverine, simetride, sodium salicylate, sulfamipyrine, suprofen, talniflumate, tenoxicam, terofenamate, tetradrine, tinoridine, tolfenamic acid, tolpronine, tramadol, viminol, xenbucin, zomepirac, and pharmaceutically acceptable salts thereof.

Exemplary local anesthetic therapeutic agents include, but are not limited to, ambucaine, amolanone, amylocaine hydrochloride, benoxinate, benzocaine, betoxycaine, biphenamine, bupivacaine, butacaine, butaben, butanilicaine, butethamine, butoxycaine, carticaine, chloroprocaine hydrochloride, cocaethylene, cocaine, cyclomethycaine, dibucaine hydrochloride, dimethisoquin, dimethocaine, diperadon hydrochloride, dyclonine, ecgonidine, ecgonine, ethyl chloride, beta-eucaine, euprocin, fenalcomine, fomocaine, hexylcaine hydrochloride, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine hydrochloride, phenol, piperocaine, piridocaine, polidocanol, pramoxine, prilocaine, procaine, propanocaine, proparacaine, propipocaine, propoxycaine hydrochloride, pseudococaine, pyrrocaine, ropavacaine, salicyl alcohol, tetracaine hydrochloride, tolycaine, trimecaine, zolamine, and pharmaceutically acceptable salts thereof.

Exemplary antispasmodic therapeutic agents include, but are not limited to, alibendol, ambucetamide, aminopromazine, apoatropine, bevonium methyl sulfate, bietamiverine, butaverine, butropium bromide, n-butylscopolammonium bromide, caroverine, cimetropium bromide, cinnamedrine, clebopride, coniine hydrobromide, coniine hydrochloride, cyclonium iodide, difemerine, diisopromine, dioxaphetyl butyrate, diponium bromide, drofenine, emepronium bromide, ethaverine, feclemine, fenalamide, fenoverine, fenpiprane, fenpiverinium bromide, fentonium bromide, flavoxate, flopropione, gluconic acid, guaiactamine, hydramitrazine, hymecromone, leiopyrrole, mebeverine, moxaverine, nafiverine, octamylamine, octaverine, oxybutynin chloride, pentapiperide, phenamacide hydrochloride, phloroglucinol, pinaverium bromide, piperilate, pipoxolan hydrochloride, pramiverin, prifinium bromide, properidine, propivane, propyromazine, prozapine, racefemine, rociverine, spasmolytol, stilonium iodide, sultroponium, tiemonium iodide, tiquizium bromide, tiropramide, trepibutone, tricromyl, trifolium, trimebutine, n,n-1trimethyl-3,3-diphenylpropylamine, tropenzile, trospium chloride, xenytropium bromide, and pharmaceutically acceptable salts thereof.

Figure 2A:
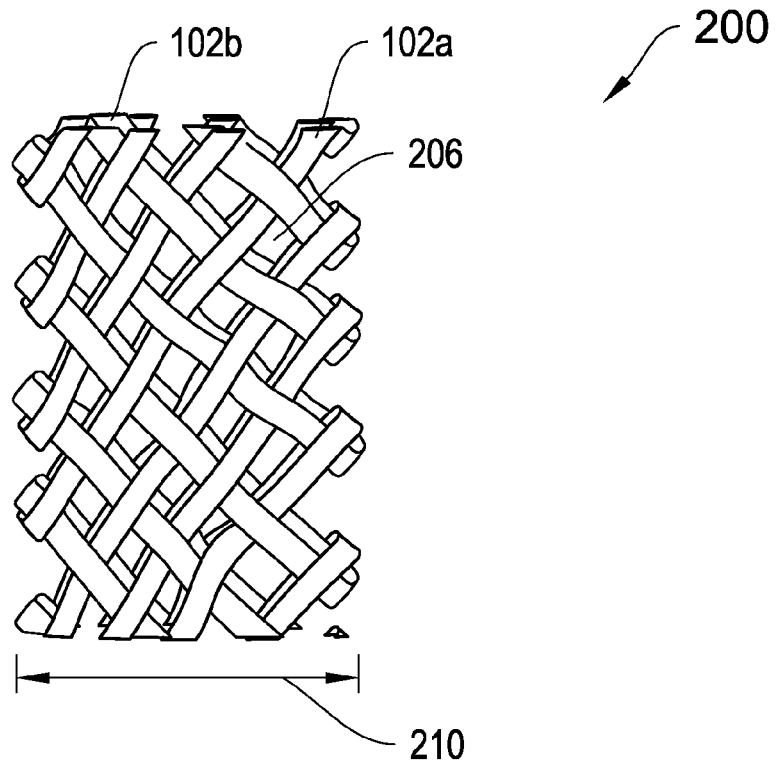
FIG. 2A is a top view of a two layer implantable mesh sling formed by flattening the tubular mesh material of FIG. 1A according to an illustrative embodiment of the invention.
Figure 2B:
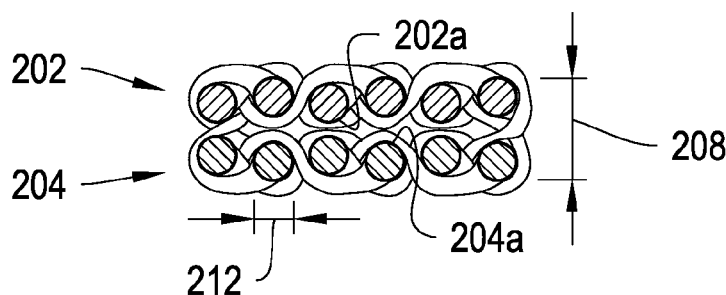
FIG. 2B is an end view of the two layer flattened mesh sling of FIG. 2A.

FIG. 2A is a top view of the mesh tube 100 flattened into an implantable supportive sling 200. FIG. 2B is an end view of the sling 200. Referring to both FIGS. 2A and 2B, and with continued reference to FIGS. 1A and 1B, the sling 200 has a top layer 202 and a bottom layer 204. The sling 200 also includes pores/interstitial gaps 206 located between the fibers 102. According to various configurations, the pores/interstitial gaps 206 extend all the way through the sling and are greater than about 25 micrometers (µm), and in some cases greater than 50 µm, or greater than about 75 µm subsequent to flattening. According to the illustrative embodiment, the sling 200 has a thickness 208 of between about 0.1 mm and about 2 mm. In some instances, the sling 200 has thickness 208 of between about 0.2 mm and about 1 mm. According to various constructions, the flattened sling may have a width 210 of between about 0.5 cm and about 1 cm, between about 1 cm and about 4 cm, between about 4 cm and about 6 cm, between about 6 cm and about 8 cm, or larger, depending on the anatomical location to be supported. The length of the sling may be cut to any desired size.

The mesh tube 100 may be flattened in any suitable manner to form the sling 200. In one process, the two mesh layers are flattened into contact with each other. However, in another embodiment, the flattening process positionally sets/fixes the top 202 and bottom 204 layers so that they do not move relative to each other. In certain embodiments, the fibers 102a of the top layer 202 do not precisely align with the fibers 102b of the bottom layer 204 when the tubular sling material 100 is flattened into the sling 200. Instead, in such embodiments, the fibers 102a and 102b overlap in a non-uniform and irregular fashion.

According to one process, the mesh tube 100 is pressed at sufficient pressure to flatten and to set/fix the top 202 and bottom 204 layers together. In some instances, the pressure applied during pressing is sufficient to cause the fiber width 212 subsequent to pressing to be greater than the fiber width 104 prior to pressing. In a further process, the mesh tube 100 is sufficiently heated during, prior to, or subsequent to the pressing process to heat bond the inner sides 202a and 204a of the top 202 and bottom 204 layers together. In an alternative process, an adhesive is placed between the top 202 and bottom 204 layers and/or on one or more of the fibers 102 prior to pressing to bond the layers 202 and 204 together.

As mentioned above, the sling 200 formed from flattening the mesh tube 100 has numerous advantages over prior art implantable slings. For example, by selecting a mesh tube 100 of correct diameter, the sling 200 may be formed with any desirable width 210, without the need for any additional cutting. By avoiding mesh cutting, formation of tanged/jagged edges is also avoided. Additionally, by flattening the mesh tube 100 to form the sling 200, the sling 200 retains the important feature of having interstitial gaps/pores 206 (which promote tissue in growth), without creating the problem of jagged/tanged long edges.

According to another advantage and as mentioned above, flattening the top 202 and bottom 204 layers together causes the fibers 102a and 102b, respectively, of those layers to overlap in a non-uniform, irregular manner. With the fibers 102a and 102b unaligned and bonded, the sling 200 is less likely to stretch than single layer mesh slings. The reduced stretchability of the sling 200 relative to single layer mesh sling counterparts also makes it less likely to twist, narrow or otherwise deform in an undesirable fashion during implantation into the body of a patient. According to a further advantage of the invention, this structural property is achieved without having to knit, braid or otherwise form the sling material 100 using a complicated fiber arrangement, such as using axially parallel fibers or periodic radially extending cross fibers, as may be needed with single layer mesh slings.

Figure 3:
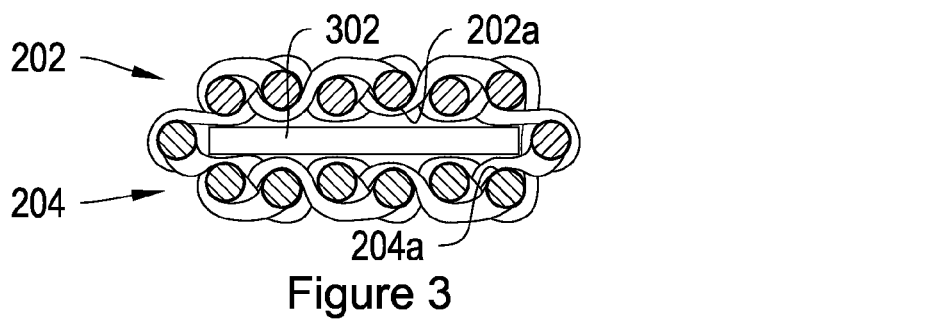
FIG. 3 is an end view of a three layer implantable mesh sling formed by locating a film or other layer of material inside the tubular mesh material of FIG. 1A prior to flattening it according to another illustrative embodiment of the invention.

FIG. 3 shows a further illustrative sling embodiment 300 in which a film material 302 is disposed between the top 202 and bottom 204 layers prior to flattening. The film 302 may be formed from any suitable material and may be biodegradable and/or bioabsorbable. Additionally, it may be treated with any of the above described agents, including without limitation, anti-inflammatory agents, including steroidal and non-steroidal anti-inflammatory agents, analgesic agents, including narcotic and non-narcotic analgesics, local anesthetic agents, antispasmodic agents, growth factors, gene-based therapeutic agents, antibiotics and combinations thereof. The film 302 may also be treated with an adhesive, which may be heat activated, or itself may be formed from a heat activated adhesive for aiding in bonding the top 202 and bottom 204 sling layers.

The multilayer sling 200/300 of the invention may also include a sleeve for covering it, at least partially, during implantation. The sleeve may be made, for example, from one or more absorbent materials, such as a sponge-like material, that can optionally be pre-soaked in a drug solution, for example, in an anesthetic, anti-inflammatory, coagulating, anticoagulating, or antibiotic solution. In another embodiment, the sleeve may be made from a non-wettable material, such as polypropylene, polyethylene, polyester, polytetrafluoroethylene (available from DuPont Corporation, Wilmington, Del., under the trademark TEFLON®), TYVEK®, MYLAR®, or co-polymers thereof. The non-wettable materials can also be pretreated with a therapeutically effective drug coating. The sleeve is preferably transparent so that an operator will be able to see the implantable, tubular sling inside the sleeve.

According to another feature, the sling 200/300 of the invention may include any suitable end portions, such as tissue dilators, anchors, and association mechanisms for associating the sling with a delivery device. Without limitation, examples of slings, sling assemblies, sling delivery devices and approaches, sling assembly-to-delivery device association mechanisms, and sling anchoring mechanisms including features with which the sling of the invention may be employed are disclosed in U.S. Pat. No. 6,042,534, entitled "Stabilization sling for use in minimally invasive pelvic surgery," U.S. Pat. No. 6,755,781, entitled "Medical slings," U.S. Pat. No. 6,666,817, entitled "Expandable surgical implants and methods of using them," U.S. Pat. No. 6,042, 592, entitled "Thin soft tissue surgical support mesh," U.S. Pat. No. 6,375,662, entitled "Thin soft tissue surgical support mesh," U.S. Pat. No. 6,669,706, entitled "Thin soft tissue surgical support mesh," U.S. Pat. No. 6,752,814, entitled "Devices for minimally invasive pelvic surgery," U.S. Ser. No. 10/918,123, entitled "Surgical Slings," U.S. patent application Ser. No. 10/641,376, entitled "Spacer for sling delivery system," U.S. patent application Ser. No. 10/641,192, entitled "Medical slings," U.S. Ser. No. 10/641,170, entitled "Medical slings," U.S. Ser. No. 10/640,838, entitled "Medical implant," U.S. patent application Ser. No. 10/460,112, entitled "Medical slings," U.S. patent application Ser. No. 10/631,364, entitled "Bioabsorbable casing for surgical sling assembly," U.S. Ser. No. 10/092,872, entitled "Medical slings," U.S. patent application Ser. No. 10/939,191, entitled "Devices for minimally invasive pelvic surgery," U.S. patent application Ser. No. 10/774,842, entitled "Devices for minimally invasive pelvic surgery," U.S. patent application Ser. No. 10/774,826, entitled "Devices for minimally invasive pelvic surgery," U.S. Ser. No. 10/015,114, entitled "Devices for minimally invasive pelvic surgery," U.S. patent application Ser. No. 10/973,010, entitled "Systems and methods for sling delivery and placement," U.S. patent application Ser. No. 10/957,926, entitled "Systems and methods for delivering a medical implant to an anatomical location in a patient," U.S. patent application Ser. No. 10/939,191, entitled "Devices for minimally invasive pelvic surgery," U.S. patent application Ser. No. 10/918,123, entitled "Surgical slings," U.S. patent application Ser. No. 10/832,653, entitled "Systems and methods for sling delivery and placement," U.S. patent application Ser. No. 10/642,397, entitled "Systems, methods and devices relating to delivery of medical implants," U.S. patent application Ser. No. 10/642,395, entitled "Systems, methods and devices relating to delivery of medical implants," U.S. patent application Ser. No. 10/642,365, entitled "Systems, methods and devices relating to delivery of medical implants," U.S. patent application Ser. No. 10/641,487, entitled "Systems, methods and devices relating to delivery of medical implants," U.S. patent application Ser. No. 10/094,352, entitled "System for implanting an implant and method thereof," U.S. patent application Ser. No. 10/093,498, entitled "System for implanting an implant and method thereof," U.S. patent application Ser. No. 10/093,450, entitled "System for implanting an implant and method thereof," U.S. patent application Ser. No. 10/093,424, entitled "System for implanting an implant and method thereof," U.S. patent application Ser. No. 10/093,398, entitled "System for implanting an implant and method thereof," and U.S. patent application Ser. No. 10/093,371, entitled "System for implanting an implant and method thereof," the entire contents of all of which are incorporated herein by reference.

What is claimed is:

1. A multilayer implantable mesh sling comprising a longitudinally extending tubular mesh material flattened to form a mesh top layer including a first plurality of fibers and a top inner side, and a mesh bottom layer including a second plurality of fibers and a bottom inner side, the mesh top inner side being positionally fixed to the mesh bottom inner side, and the first and second pluralities of fibers overlapping non-uniformly.

2. The implantable mesh sling of claim 1, wherein the top and bottom inner sides are heat bonded together.

3. The implantable mesh sling of claim 1, wherein the top and bottom inner sides are pressure bonded together.

4. The implantable mesh sling of claim 1, wherein the top and bottom inner sides are adhesive bonded together.

5. The implantable mesh sling of claim 1 including a middle layer disposed between the top and bottom layers, the middle layer including an agent.

6. The implantable mesh sling of claim 5, wherein the agent is a therapeutic agent.

7. The implantable mesh sling of claim 5, wherein the middle layer is biodegradable.

8. The implantable mesh sling of claim 1 including a plurality of interstitial gaps of about 25 µm extending through both the top and bottom layers.

9. The implantable mesh sling of claim 1 including a plurality of interstitial gaps of about 50 µm extending through both the top and bottom layers.

10. The implantable mesh sling of claim 1 including a plurality of interstitial gaps of about 75 µm extending through both the top and bottom layers.

11. A multilayer implantable mesh sling comprising a longitudinally extending tubular mesh material flattened to form a mesh top layer including a first plurality of fibers and a top inner side, and a mesh bottom layer including a second plurality of fibers and a bottom inner side, the mesh top inner side contacting the mesh bottom inner side, and the first and second pluralities of fibers overlapping non-uniformly.

* * * * *